United States Patent [19]

Lam

[11] Patent Number: 4,684,759
[45] Date of Patent: Aug. 4, 1987

[54] PROCESS FOR RECOVERING ENERGY FROM AN ETHANE-RICH RECYCLE STREAM

[75] Inventor: Wilfred K. Lam, Arcadia, Calif.

[73] Assignee: C. F. Braun & Co., Alhambra, Calif.

[21] Appl. No.: 768,956

[22] Filed: Aug. 23, 1985

[51] Int. Cl.$^4$ .............................................. C07C 4/02
[52] U.S. Cl. .................................. 585/652; 585/650; 585/654; 585/655
[58] Field of Search ............... 585/654, 655, 648, 650, 585/651, 652

[56] References Cited

U.S. PATENT DOCUMENTS 2,588,323  3/1952  Kniel ................................... 585/650
2,905,734  9/1959  Davison et al. ..................... 585/655

FOREIGN PATENT DOCUMENTS 1011518  12/1965  United Kingdom ............... 585/650
1102826   2/1968  United Kingdom ............... 585/650

OTHER PUBLICATIONS

Kirk-Othmer, "Encyclopedia of Chemical Technology" vol. 8, pp. 510–514 (1965 Edition).
Kister et al., "Hydrocarbon Processing", Jan. 1984, pp. 105–108.
Eng et al., "Hydrocarbon Processing", Mar. 1984, pp. 83–88.
Perry "Chemical Engineers' Handbook", 5th Edition, pp. 12–20 (1973).

Primary Examiner—Asok Pal
Attorney, Agent, or Firm—Lyon & Lyon

[57] ABSTRACT

An ethane-rich stream is reduced in pressure below the inlet pressure to a pyrolysis furnace, vaporized in heat exchange relationship with a process stream, recompressed, and passed to the pyrolysis furnace.

56 Claims, 6 Drawing Figures

FIG_1.

FIG_2

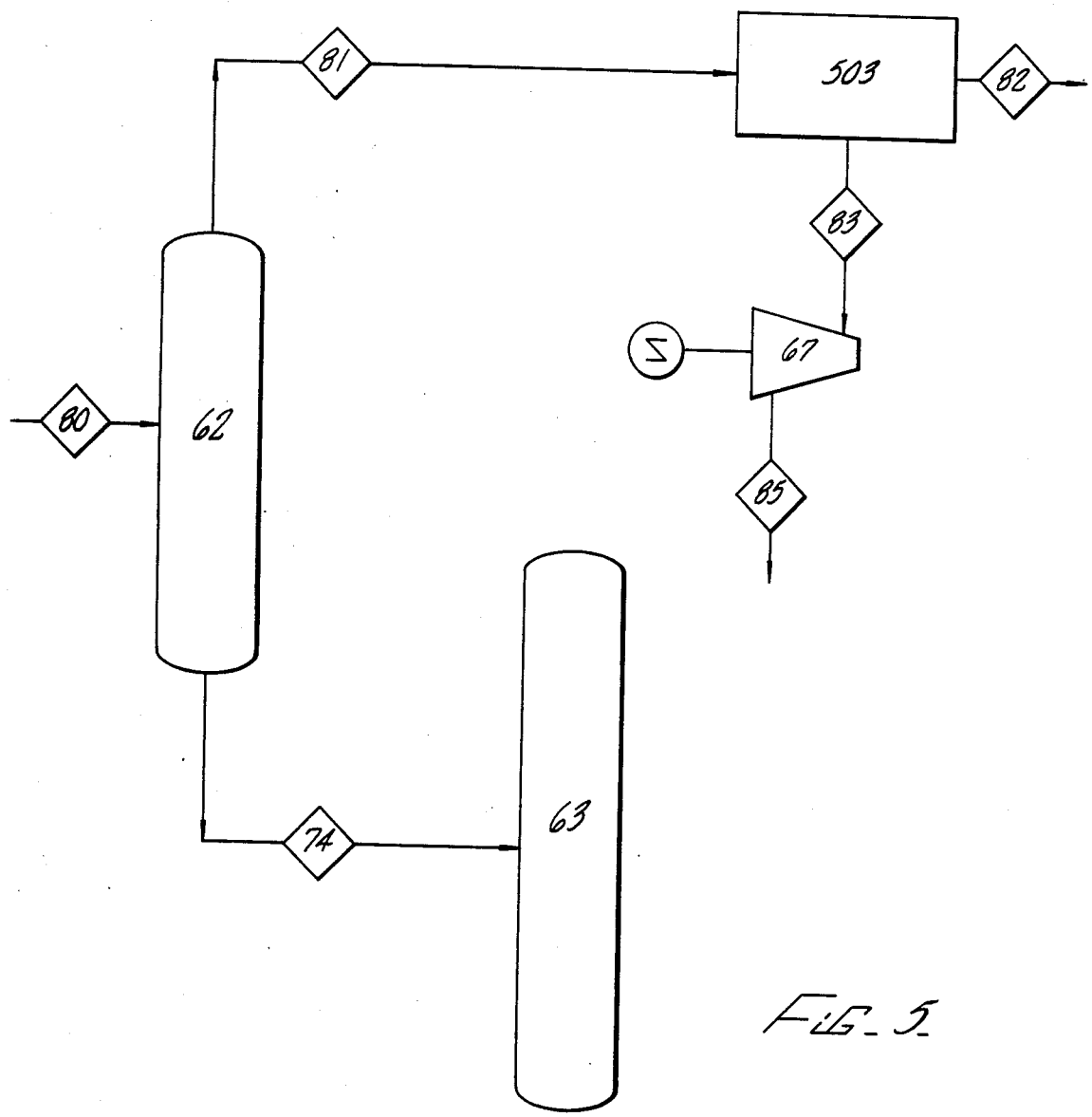
FIG_5.

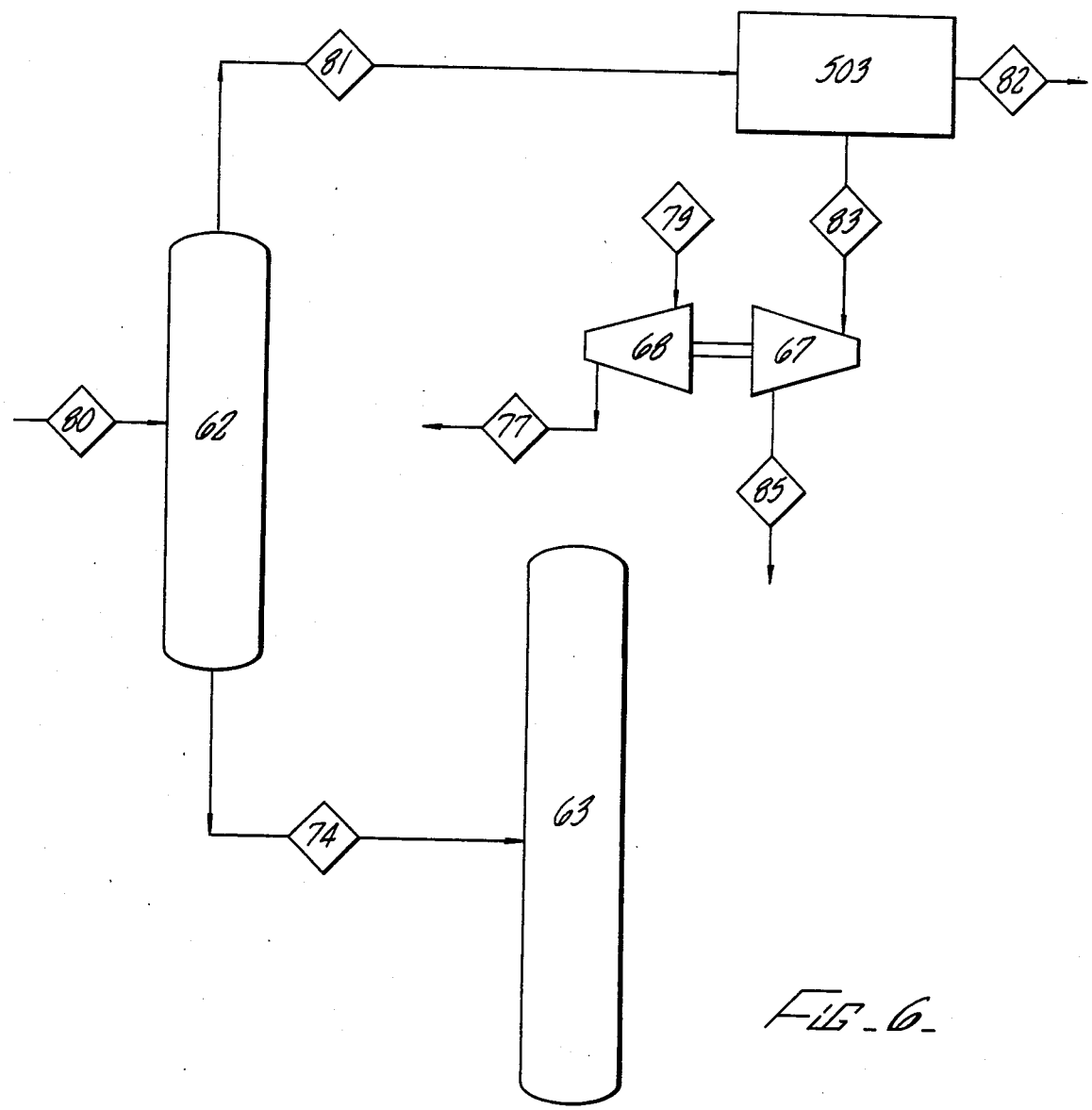
FIG_6_

PROCESS FOR RECOVERING ENERGY FROM AN ETHANE-RICH RECYCLE STREAM

BACKGROUND OF THE INVENTION

1. Field of the Invention

This invention relates to a process for recovering energy from an ethane-rich stream flowing into a pyrolysis furnace, and in particular, to a process for recovering energy from an ethane recycle stream collected from the bottom of an ethylene-ethane splitter.

2. Description of the Prior Art

Ethylene is an important chemical in the petrochemical industry, particularly in the production of polymers. Ethylene may be obtained through separation processes from hydrocarbon mixtures which are derived from various sources such as normal refinery operations, cracking processes and the like. The content of the hydrocarbon mixture containing ethylene will vary depending upon the source of the hydrocarbon mixture. However, it is typical that a hydrocarbon mixture used in an ethylene production plant will include hydrogen, methane, ethane, ethylene and other higher hydrocarbons.

In general, an ethylene plant produces ethylene and by-products by pyrolysis reactions which take place in pyrolysis furnaces. The feedstock used may be ethane, propane, butane, naphtha, heavier hydrocarbons, or any combination of these. The stream leaving the pyrolysis furnace is comprised of ethylene, lighter by-products, heavier by-products and unreacted feedstock. The stream leaving the pyrolysis furnace is cooled compressed then separated into various product streams. The main product stream is the ethylene product. Typical by-product streams are propylene, hydrocarbons, gasoline, fuel oil, fuel gas, hydrogen, ethane and propane. Of these, ethane and propane are valuable as pyrolysis furnace feedstocks, and are usually recycled to the pyrolysis furnaces and cracked to extinction to produce additional ethylene. The section of an ethylene plant in which the various products and by-products are separated is referred to as the fractionation section. The fractionation section almost always includes a demethanizer, deethanizer, and an Ethylene-ethane splitter ($C_2$ splitter). Other fractionation columns such as a depropanizer, a debutanizer, a propane-propylene splitter and others are often also included. A more detailed description of an ethylene plant, the contents of which are specifically incorporated herein by reference, is set forth in an article entitled "Ethylene from NGL feedstocks" published in the March 1984 edition of "*Hydrocarbon Processing*", pages 83–88.

The fractionation section of an olefin plant requires refrigeration to obtain fractionation. A demethanizer requires very cold refrigeration for reflux condensation, see, for example, U.S. Pat. Nos. 3,443,388 and 3,902,329, the disclosures of which are incorporated herein by reference. The separation of ethylene from ethane also requires refrigeration for reflux condensation, see, for example, U.S. Pat. No. 3,320,754, the disclosure of which is incorporated herein by reference.

The refrigeration required by the fractionation and the compression sections of an ethylene plant is normally provided by cascade refrigeration system. In such a system, process chilling requirements are provided by two or more different refrigeration fluids, one providing chilling at warmer temperatures, the other providing chilling at colder temperatures. In a typical ethylene plant, a higher temperature refrigerant such as propylene refrigerant provides chilling in the temperature range of ambient to about −45° F., and a lower temperature refrigerant such as ethylene refrigerant provides chilling in the temperature range of about −45° F. to about −150° F. Heat absorbed by the lower temperature refrigerant is removed by the higher temperature refrigerant, while heat absorbed by the higher temperature refrigerant is removed by cooling water or air. The refrigeration energy for each refrigerant fluid is provided by a multi-stage refrigeration compressor.

In a typical ethylene plant, the ethylene-ethane fractionating column, commonly termed the $C_2$ splitter, is one of the major consumers of refrigeration energy. Refrigeration to this column is supplied either by the higher temperature refrigerant, or by the lower temperature refrigerant. When ethylene is the low-temperature refrigerant, and is used to supply the $C_2$ splitter refrigeration energy, the ethylene refrigeration system can be integrated with the $C_2$ splitter overhead system. A more detailed description of a $C_2$ splitter and its refrigeration system, the contents of which are specifically incorporated herein by reference, is set forth in an article entitled "Ethylene from NGL Feedstocks-Low Pressure $C_2$ Splitter", published in Jan., 1984 edition of "*Hydrocarbon Processing*", pages 105–108.

Since the $C_2$ splitter is a major consumer of refrigeration energy, significant reduction of refrigeration consumption, or recovery of refrigeration energy from this column or its auxiliaries, can significantly lower the consumption of energy in the plant, and the cost of power and refrigeration equipment in an ethylene plant.

The bottom product from the $C_2$ splitter is the ethane-rich stream which leaves the $C_2$ splitter as chilled liquid and is recycled to the pyrolysis furnaces. On route to the furnaces, refrigeration energy is recovered from the ethane-rich stream at pressures higher than the pyrolysis furnace inlet pressure. The ethane rich stream is expanded, vaporized and superheated as described below.

The ethane-rich stream leaving the bottom of the $C_2$ splitter is expanded to a pressure just above the pyrolysis furnaces inlet pressure, usually by expansion across a valve. The expansion causes the ethane-rich stream to chill to its boiling point at a pressure just above the pyrolysis furnace inlet pressure. The ethane-rich stream is then vaporized by chilling a process or refrigeration stream, a process in which most of the refrigeration energy is recovered. The ethane-rich stream may then be superheated, a process in which the rest of its refrigeration energy is recovered, and then flows into the pyrolysis furnace.

A similar refrigeration energy recovery system is employed when a liquid ethane-rich stream from an alternative source is used to feed the pyrolysis furnace. The stream is expanded to a pressure just above the pyrolysis furnace pressure, and then vaporized by chilling a process or refrigeration stream, a process in which most of its refrigeration energy is recovered. It may then be superheated, a process in which the rest of its refrigeration energy is recovered and then flows into the pyrolysis furnace.

Accordingly, enhancing the refrigeration energy recovery from the ethane-rich stream leaving the bottom of a $C_2$ splitter, as well as enhancing the refrigeration energy recovery from any other liquid ethane-rich streams which are used to feed a pyrolysis furnace, can substantially reduce the cost of refrigeration energy and refrigeration equipment in an ethylene plant.

SUMMARY OF THE INVENTION

The present invention relates to a process for recovering energy from an ethane-rich stream flowing into a pyrolysis furnace, where the energy recovery takes place at a pressure lower than the furnace inlet pressure. In this process, the ethane stream is expanded, vaporized, and recompressed.

The temperature to which a liquid or two-phase ethane-rich stream can be chilled upon expansion is determined by the pressure to which the stream is expanded, so that the lower this pressure is, the lower the temperature reached upon chilling. Present technology does not allow pressure lower than the pyrolysis furnace inlet pressure to be used in the expansion process. The invention allows a pressure considerably lower than pyrolysis furnace inlet pressure to be achieved upon expansion. Because of this lower pressure, the ethane-rich stream can be chilled to a considerably lower temperature. This enables ethane vaporization, and therefore, refrigeration energy recovery at a lower temperature. Recovering refrigeration energy at a lower temperature enables significant reduction in refrigeration energy consumption. The saving of refrigeration energy consumption creates a net energy gain even though the expanded ethane-rich stream must then be compressed to a pressure sufficient to allow it to be passed to the pyrolysis furnace. Thus, the reduction in refrigeration energy consumption leads to significant savings in capital and operating costs, and these can be realized by applying the present invention to an ethylene plant design.

In another aspect of the invention, the recompression step preheats the ethane-rich stream before it enters the furnace. The preheat reduces the amount of heating requirements of the pyrolysis furnace, thus making furnace heat available for alternative purposes, such as preheating boiler feedwater, which in turn, increases steam generation at the pyrolysis furnace waste heat boilers.

In another aspect of the invention, an ethylene plant often has a tail gas expander, the function of which is to expand the tail gas product. Energy is recovered at that expander, but is often wasted because in many cases there is no service where this energy can be applied. The ethane recompressor provides such a service, thus enabling additional energy to be recovered. The use of an expander-recompressor system can also reduce the capital cost of the recompressor, because the recompressor can share the lubricating oil and seal oil systems of the expander.

These and further objectives and advantages of the present invention will be apparent to those skilled in the art in connection with the following description of the preferred embodiment and accompanying drawings.

DESCRIPTION OF THE DRAWINGS

FIG. 5 is a flow diagram of a portion of the treatment process 500 depicted in FIG. 1; and FIG. 6 is a flow diagram of a portion of the treatment process 500 depicted in FIG. 2 according to a preferred embodiment of the present invention where the expander 67 of the treatment process 500 is utilized as a driver to the compressor 68, compressor 68 not being a part of the treatment process 500.

DESCRIPTION OF THE PREFERRED EMBODIMENTS

A preferred embodiment of the present invention is described below in connection with the design of an ethylene plant. While the present invention is particularly well suited for use in an ethylene plant, it can also be applied to other plants, such as NGL Recovery Plants, wherein an ethane-rich stream is present either as feed or product or intermediate product stream. Further, the present description has been described by comparison to an actual design of an ethylene plant constructed by the assignee of the present invention, depicted in FIG. 1. However, as would be apparent to one skilled in the art, the present invention is not limited in application to any one particular design of an ethylene plant. Rather, the description of the prior process is meant to provide a basis for comparison of the differences between the present invention and the prior art. Accordingly, where process parameters are given below, the parameters are based upon an ethylene plant with a capacity of a billion pounds per year ethylene production.

Figure 1:
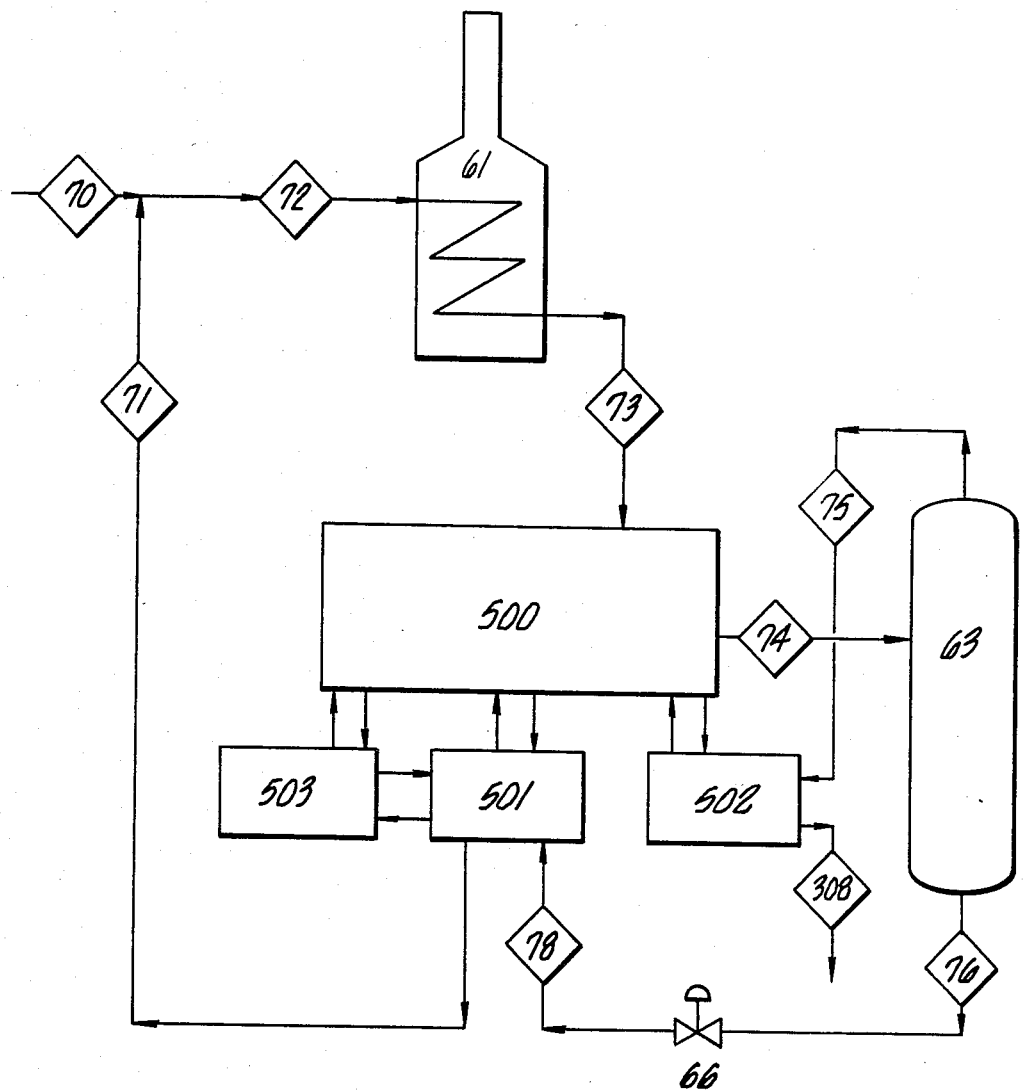
FIG. 1 is a simplified flow diagram of an ethylene plant according to the prior art.

FIG. 1 illustrates a simplified flow diagram of an ethylene plant according to the prior art. A feed stock 70, which may vary considerably as to composition, is combined with a vaporized ethane-rich recycle stream 71 to form a feed stream 72 which is passed into a pyrolysis furnace 61.

An ethylene plant generally has several pyrolysis furnaces operating in parallel. The ethane-rich recycle stream may be mixed with the rest of the plant feed, alternatively, it may enter separate pyrolysis furnaces without mixing with the rest of the feed. The feed stream 72 is at an inlet pressure which typically is around 90 psia. The feed stream 72 is cracked in the pyrolysis furnaces 61 to form a cracked gas 73 which is passed to a treatment process which is generally depicted as 500. A stream of ethylene and ethane 74 is passed to a $C_2$ splitter 63. An ethylene product stream 75 is recovered as an overhead stream from $C_2$ splitter 63 and passed to an ethylene refrigeration system generally depicted as 502. After heat exchange and or processing of ethylene product stream 75 with ethylene refrigeration system 502, an ethylene product stream 308 is recovered from the ethylene refrigeration system 502. In some plants, the $C_2$ splitter overhead system is not integrated with the refrigeration system. In such cases, the ethylene product stream 75 flows directly into the ethylene distribution headers. An ethane-rich recycle stream 76 is recovered as a $C_2$ splitter 63 bottom stream. The pressure of the $C_2$ splitter bottom stream 76 will always be at least as high, or greater than, the inlet pressure of the pyrolysis furnace 61 and will generally be in the range of about 50 to about 400 psia and most commonly in the range of 70 to 300 psia. When the $C_2$ splitter pressure is lower than the pyrolysis furnace inlet pressure, a pump is used to raise the pressure to above the furnace inlet pressure in order to enable flow from the C₂ splitter bottom to the furnace. However, since it is typical to use a centrifugal pump, the pressure at the pump discharge will normally be greater than required for introduction to the pyrolysis furnace 61. The ethane-rich recycle stream 76 is then expanded by flashing across a control valve 66 to form a chilled ethane-rich recycle stream 78. The chilled ethane-rich recycle stream 78 then flows to a vaporizer 501 where it is vaporized at a pressure greater than the pyrolysis furnace 61 inlet pressure. Vaporization takes place by heat exchange with either a process stream or a refrigerant stream. The refrigeration recovery from vaporizing the chilled ethane-rich recycle stream 78 at this temperature and pressure range is equivalent to saving of refrigerant at temperatures warmer than −50° F. Most commonly, the refrigeration saved is propylene at the −45° F. to 25° F. levels. The propylene refrigeration system is generally depicted as 503. After vaporization, the ethane-rich recycle stream 71 is further superheated either by heat exchange with other process streams or in the convection section of the pyrolysis furnace 61.

Figure 2:
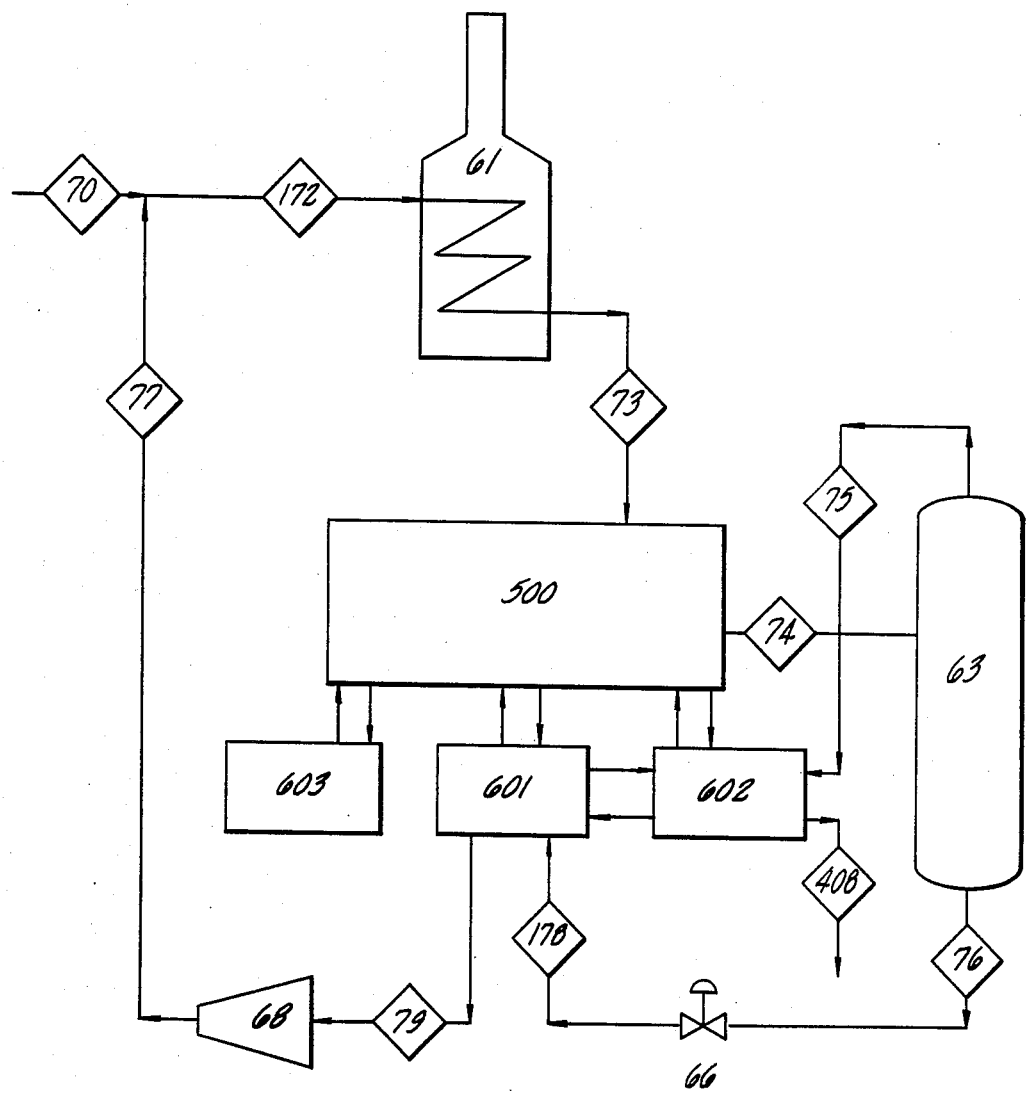
FIG. 2 is a simplified flow diagram of an ethylene plant according to the present invention.

FIG. 2 illustrates a simplified flow diagram of an ethylene plant according to a preferred embodiment of the present invention. The feed stock 70 is combined with a compressed ethane-rich recycle stream 77 to form a feed stream 172 which is passed into the pyrolysis furnaces 61. An ethylene plant generally has several pyrolysis furnaces operating in parallel. Accordingly, where a pyrolysis furnace is hereinafter described, the pyrolysis furance can represent one or more pyrolysis furnaces. The compressed ethane-rich recycle stream may be mixed with the rest of the plant feed, alternatively it may enter separate pyrolysis furnaces without mixing with the rest of the feed. The feed stream 172 is at an inlet pressure which is typically around 90 psia but may vary between the range of about 50 psia to about 130 psia. The feed stream 172 is cracked in the pyrolysis furnace 61 to form a cracked stream 73 which is passed to the treatment process, generally depicted as 500, from which a stream comprised of ethylene and ethane 74 is passed to a C₂ splitter 63. The stream comprised of ethylene and ethane will typically contain at least 90 mole percent ethylene and ethane. An ethylene product stream 75 is recovered as an overheads stream from splitter 63 and passed to an ethylene refrigeration system generally depicted as 602. A cascade refrigeration system may be used in the treatment process 500 to provide chilling. After heat exchange of ethylene product stream 75 with ethylene refrigeration system 602, an ethylene product stream 408 is recovered from the ethylene refrigeration system 602. In some plants, the C₂ splitter overhead system is not integrated with the refrigeration system. In such cases, the ethylene product stream 75 flows directly into the ethylene distribution header. An ethane-rich recycle stream 76 is recovered as a bottom stream from the C₂ splitter 63. The ethane-rich recycle stream 76 typically contains at least 80 mole percent ethane and is at a pressure between about 50 psia to about 300 psia. While the present description is directed to an ethane-rich recycle stream 76 which is recovered from a C₂ splitter in an ethylene plant in which the pyrolysis furnace is located, an ethane-rich stream could originate from a different plant than the plant in which the pyrolysis furnace is located, and one or more ethane-rich feed streams could be mixed to form the ethane-rich recycle stream 76. The ethane-rich recycle stream 76 is passed to a control valve 66 which reduces the pressure of the ethane-rich recycle stream 76 to a pressure below the inlet pressure of the pyrolysis furnace 61, the reduced pressure generally being in the range from about 14 psia to about 90 psia, thereby decreasing the temperature of the ethane-rich recycle stream 76 to form a chilled ethane-rich recycle stream 178. The chilled ethane-rich recycle stream 178 then flows to a vaporizer 601 where it is vaporized by heat exchange with a process stream to form a vaporized ethane-rich stream and a chilled process stream. The process stream can be a refrigerant stream (not shown). In a preferred embodiment, the process stream may be comprised of a demethanizer feed stream. The chilled process stream will be at a temperature lower than about −50° F. The refrigeration recovery from vaporizing the chilled ethane recycle stream 178 at this temperature and pressure range, which is considerably lower than that for the system shown in FIG. 1, is equivalent to saving of refrigerant at temperatures between −130° F. and −50° F. Most commonly, the refrigerant saved is ethylene at the −100° F. to −70° F. levels. The vaporized ethane-rich stream 79, which may optionally be mixed with another feed stream, is compressed to the inlet pressure of the pyrolysis furnace 61 by a compressor 68 to form a compressed ethane-rich stream 77 at a pressure just greater than the pyrolysis furnace 61 inlet pressure. The compressed ethane-rich stream 77 is then passed to the pyrolysis furnace 61 and the chilled process stream is utilized to reduce the overall energy consumption for the process. Although not depicted in FIG. 2, the vaporized ethane-rich stream may be superheated by heat exchange with a second process stream to form a superheated ethane-rich recycle stream and a second chilled process stream. The second process stream may be a refrigerant stream. Further, the first and the second process streams may be the same stream.

As is apparent from a comparison of FIGS. 1 and 2, the heat exchange associated with the vaporization of the ethane-rich stream 76 in the prior art was utlized to recover refrigeration at a temperature level greater than −50° F. which is typical of propylene refrigeration, whereas the heat exchange associated with the vaporization of the ethane-rich stream 76 of the present invention can be utilized in the temperature range of −130° F. to −50° F., which is typical of ethylene refrigeration. The ethylene refrigeration system is graphically depicted as 602. The advantages associated with vaporizing the ethane-rich recycle stream 178 at pressures lower than the pyrolysis furnace inlet pressure are illustrated more fully by a detailed description of propylene refrigeration systems 503 and 603 and ethylene refrigeration systems 502 and 602.

Figure 3:
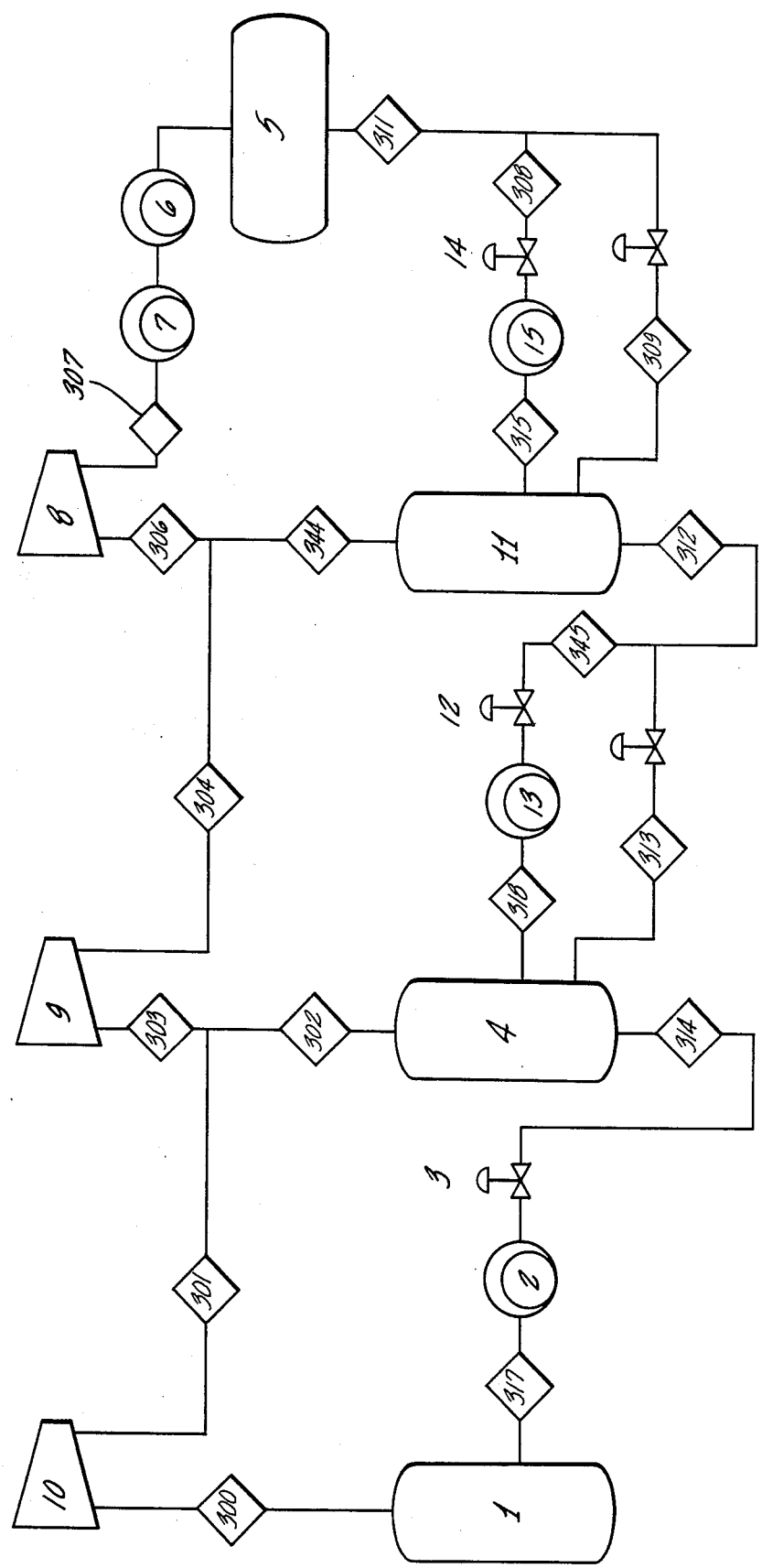
FIG. 3 is a flow diagram of the ethylene refrigeration system 502 depicted in FIG. 1 and 602 depicted in FIG. 2.

FIG. 3 is a flow diagram of a typical ethylene refrigeration system 502 depicted in FIG. 1 or 602 depicted in FIG. 2. Stream 300 from the ethylene compressor first stage suction drum 1 is sent to the inlet of an ethylene compressor first stage 10. Stream 301 from the outlet of first stage 10, combines with stream 302 from ethylene compressor second stage drum 4 to form stream 303 and is sent to the inlet of an ethylene compressor second stage 9. Stream 304 exits the outlet of second stage 9 and combines with stream 344 from the ethylene compressor third stage drum 11 to form stream 306. Stream 306 is sent to the inlet of an ethylene compressor third stage 8. Stream 307 exits the outlet of third stage 8 and is passed through ethylene desuperheater 7 and ethylene condenser 6. Stream 311 exits condenser 6 and is passed through ethylene accumulator 5. Stream 11 is split into stream 308 and stream 309. Stream 308 is controlled by valve 14 and is vaporized in heat exchanger 15. Vapor stream 315 leaving heat exchanger 15 is sent to ethylene compressor third stage drum 11. Stream 308 may be a plurality of parallel streams, with each stream using a separate valve and heat exchanger. Stream 309 is expanded to the ethylene compressor third stage drum 11. Liquid leaving the third stage ethylene compressor drum is stream 312. Stream 312 is split into stream 313 and stream 345. Stream 345 is controlled by valve 12 and vaporized in heat exchanger 13. Stream 345 may be a plurality of parallel streams, with each stream using a separate valve and heat exchanger. Stream 318 from heat exchanger 13 is passed to the second stage drum 4. Stream 313 is expanded to the second stage drum 4. Stream 314 is the liquid from second stage drum 4 is controlled by valve 3, and vaporized in heat exchanger 2. Stream 317 from heat exchanger 2 is passed to first stage suction drum 1. Stream 314 may be a plurality of parallel streams, with each stream using a separate valve and heat exchanger.

The ethylene refrigeration system described above is often integrated with the $C_2$ splitter overhead system. When such integration takes place, the overhead stream from the $C_2$ splitter normally enters the refrigeration system at the first stage drum 1, or the second stage drum 4, or joins the vapor stream from one of these drums. $C_2$ splitter reflux is then withdrawn either from the ethylene accumulator 5, or from the third stage drum 11, or from the second stage drum 4, or from the liquid stream leaving of these drums. An ethylene product stream is withdrawn either from the compressor third stage discharge stream 307 or from the accumulator liquid stream 311 or from the accumulator 5. Reboil to the $C_2$ splitter is supplied by a vapor stream withdrawn either from the compressor third stage suction stream 306, or from the third stage discharge stream 307, or from the desuperheated third stage discharge stream leaving desuperheater 7. This vapor steam is condensed in the $C_2$ splitter reboiler, and returned either to the accumulator 5, or to the third stage drum 11, or combined with the liquid streams leaving one of these drums.

A liquid subcooler may sometimes be incorporated with the ethylene refrigeration system. When such incorporation takes place, a liquid stream is withdrawn from the accumulator 5, chilled by heat exchange with a process stream, and the chilled liquid is returned to the second stage drum 4, or the third stage drum 11, or the liquid stream leaving one of these drums.

Figure 4:
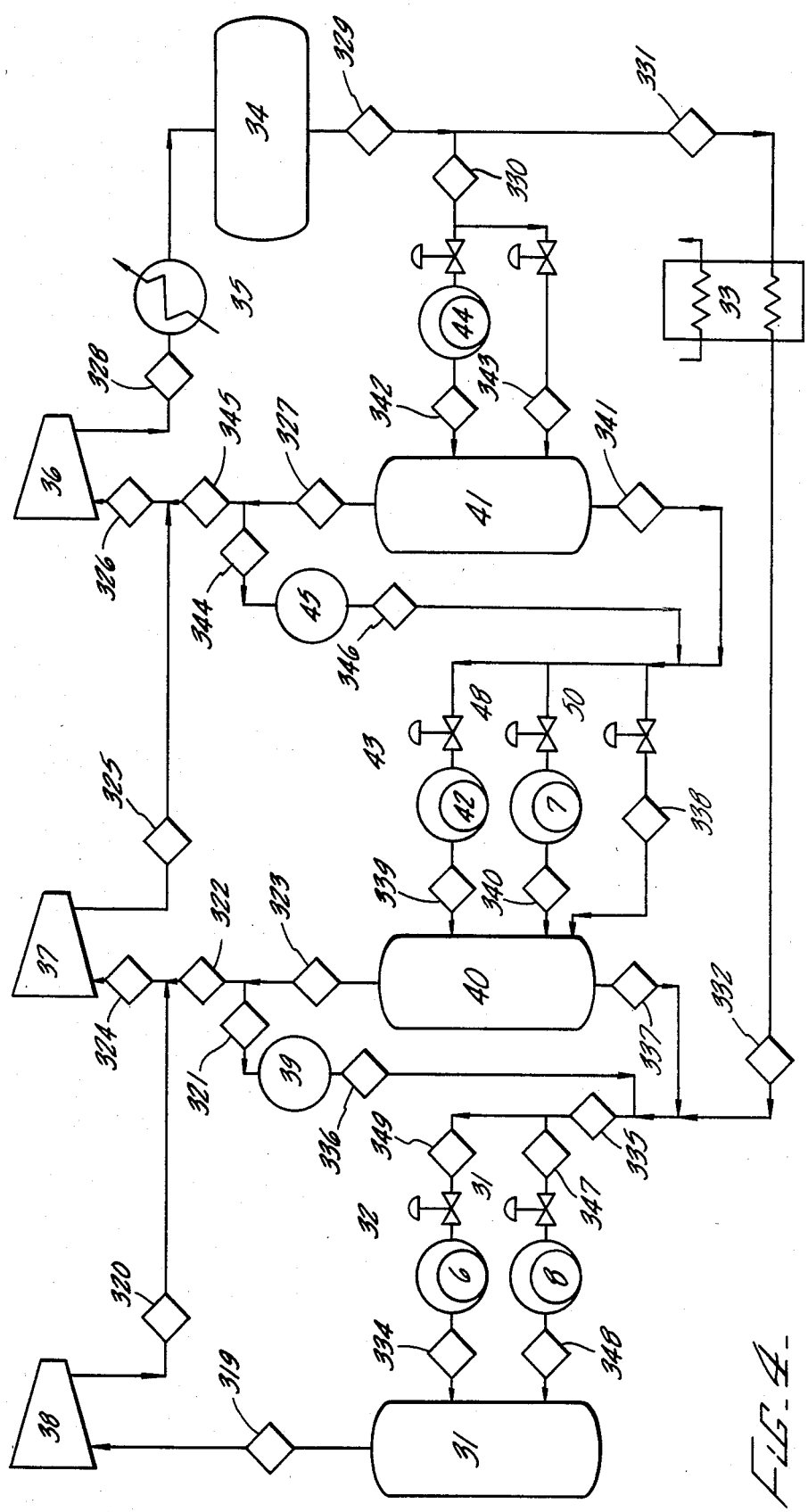
FIG. 4 is a flow diagram of the propylene refrigeration system 503 depicted in FIG. 1 and 603 depicted in FIG. 2.

FIG. 4 is a flow diagram of a typical propylene refrigeration system 503 depicted in FIG. 2. Propylene is recirculated in a closed system. Stream 319 is sent from propylene compressor first stage suction drum 31 to the inlet of propylene compressor first stage 38. Stream 320 exits from the outlet of first stage 38. Stream 323 from propylene compressor second stage suction drum 40 is split into streams 321 and 322. Stream 321 is passed to a heat recovery heat exchanger 39. Stream 321 may be a plurality of parallel streams, with each stream using a separate heat exchanger. Stream 322 is combined with stream 320 to form stream 324 which is sent to the inlet of propylene compressor second stage 37. Stream 327 from the propylene compressor third stage suction is split into streams 344 and 345. Stream 344 is passed to a heat recovery heat exchanger 45. Stream 344 may be a plurality of parallel streams, with each stream using a separate heat exchanger. Stream 325 exits the outlet of second stage 37 and is combined with stream 345 to form stream 326 which is sent to the inlet of propylene compressor third stage 36. Stream 328 exits the outlet of third stage 36 and is condensed in propylene condenser 35 to form stream 329 which is passed to propylene accumulator 34. Stream 329 exiting propylene accumulator 34 is split into streams 330 and 331. Stream 331 is passed to subcooler 33. Stream 331 may be a plurality of parallel streams, with each stream using a separate heat exchanger. Subcooled liquid from these different heat exchangers may be returned to different points in the refrigeration system. Stream 330 is split into streams 342 and 343. Stream 342 is controlled by a valve and vaporized in heat exchangers 44. Stream 342 may be a plurality of parallel streams, with each stream using a separate valve and heat exchanger. Vaporized stream 342 from heat exchanger 44 is passed to third stage suction drum 41. Stream 343 is also passed to third stage suction drum 41. Stream 341 from third stage suction drum 41 is combined with stream 346 from the heat recovery exchanger 45 and is split into streams 338, 339 and 340. Stream 339 is controlled by valve 43 and vaporized in heat exchangers 42. Stream 339 may be a plurality of parallel streams, with each stream using a separate valve and heat exchanger. Vaporized stream 339 from heat exchanger 42 is passed to second stage drum 40. Stream 340 is controlled by valve 48 and vaporized in ethylene desuperheater 7, and the vaporized stream 340 flows to second stage suction drum 40. Stream 338 is controlled by valve 50 and passed to second stage suction drum 40. Stream 337 from second stage suction drum 40 is combined with stream 332 from subcooler 33 and stream 336 from heat recovery exchangers 39 to form stream 335. Stream 335 is split into streams 347 and 349. Stream 347 is controlled by valve 31 and is vaporized in heat exchanger 8. Stream 347 may be a plurality of parallel streams, with each stream using separate valve and heat exchanger. Vaporized stream 348, from heat exchanger 8 is passed to first stage drum 31. Stream 349 is controlled by valve 32 and is vaporized in ethylene condenser 6 to form stream 334 which is passed to first stage suction drum 31.

In order to further facilitate an understanding of the present invention, the application of the invention will be illustrated in the example that follows in which a design using the conventional technology is compared to a design using the invention. The designs are based on a plant producing 1 billion LB/yr. ethylene from ethane feedstock. Table 1 defines the process conditions along the route of the ethane recycle stream from the bottom of the $C_2$ splitter to the pyrolysis furnace using the conventional technology. Referring to FIG. 1, in this design the bottom stream 76 of the $C_2$ splitter 63 is pumped to above the pyrolysis furnace pressure, then expanded across valve 66. It is then vaporized and superheated in a vaporizer and a superheater depicted as 501. Refrigeration energy is recovered in both. Vaporization takes place by heat exchange with the deethanizer overhead stream, which recover propylene refrigeration at the $-40°$ F. propylene refrigeration level. Superheating takes place by recovering propylene refrigeration energy at the $-40°$ F. and warmer propylene refrigeration levels. Table 3 calculates the refrigeration horsepower saved by recovering the refrigeration energy, using the calculation procedure published by Y.R. Mehra in "Chemical Engineering", the disclosures of which are specifically incorporated herein by reference, parts 1 to 3, (Dec. 18, 1978 issue page 97; Jan. 15, 1979 issue page 131; Feb. 12, 1979 issue page 95). The superheated ethane recycle stream 71 flows to the pyrolysis furnace.

Table 2 defines the process conditions along the route of the ethane recycle stream from the bottom of the $C_2$ splitter to the pyrolysis furnace using the invention. Referring to FIG. 2, in this design the bottom stream 76 of the $C_2$ splitter 63 is expanded across valve 66. It is then vaporized and superheated in a vaporizer and superheater depicted as 601. Refrigeration energy is recovered in both. Vaporization takes place by heat exchange with the demethanizer feed stream, which recovers ethylene refrigeration energy at $-75°$ F. and propylene refrigeration energy at all the propylene refrigeration temperature levels. Table 3 calculates the refrigeration horsepower saved by recovering the refrigeration energy using the method cited above. The superheated ethane recycle stream 78 is then compressed by recompressor 68 to become the recompressed ethane recycle stream 77 which flows to the pyrolysis furnace 61.

TABLE 1

| Stream No. | Description | Stream Composition, MOL % | | | Flow Rate LB MOL/H | Flow Rate LB/HR | Temp. °F. | Pressure psIA | Vapor MOL % |
|---|---|---|---|---|---|---|---|---|---|
| | | Ethylene | Ethane | Propylene | | | | | |
| 76 | $C_2$ Splitter Bottom, Exit $C_2$ Splitter | 0.8 | 98.5 | 0.7 | 3448 | 103,910 | −63 | 74 | 0 |
| 76 | $C_2$ Splitter Bottom, Exit Bottom Pump | 0.8 | 98.5 | 0.7 | 3448 | 103,910 | −63 | 110 | 0 |
| 78 | $C_2$ Splitter Bottom, At Vaporizer Inlet | 0.8 | 98.5 | 0.7 | 3448 | 103,910 | −63 | 101 | 0 |
| 71 | Ethane Recycle, Exit Vaporizer | 0.8 | 98.5 | 0.7 | 3448 | 103,910 | −46 | 98 | 100 |
| 71 | Ethane Recycle, Exit Superheater | 0.8 | 98.5 | 0.7 | 3448 | 103,910 | 75 | 93 | 100 |

TABLE 2

| Stream No. | Description | Stream Composition, MOL % | | | Flow Rate LB MOL/H | Flow Rate LB/H | Temp. °F. | Pressure psIA | Vapor MOL % |
|---|---|---|---|---|---|---|---|---|---|
| | | Ethylene | Ethane | Propylene | | | | | |
| 76 | $C_2$ Splitter Bottom, Exit Tower | 0.8 | 98.5 | 0.7 | 3448 | 103,910 | −63 | 74 | 0 |
| 78 | $C_2$ Splitter Bottom, After Flashing | 0.8 | 98.5 | 0.7 | 3448 | 103,910 | −76 | 55 | 4 |
| 79 | Ethane Recycle, Exit Vaporizer | 0.8 | 98.5 | 0.7 | 3448 | 103,910 | −77 | 52 | 100 |
| 79 | Ethane Recycle, Exit Superheater | 0.8 | 98.5 | 0.7 | 3448 | 103,910 | 75 | 47 | 100 |
| 77 | Ethane Recycle, Exit Compressor | 0.8 | 98.5 | 0.7 | 3448 | 103,910 | 151 | 93 | 100 |

TABLE 3

| | | Conventional | Invention | Source |
|---|---|---|---|---|
| 1. | Ethane Recycle Vaporization Pressure, PSIA | 98 | 52 | Table 1 and 2 |
| 2. | Ethane Recycle Vaporization Temperature, °F. | −46 | −77 | Table 1 and 2 |
| 3. | Refrigeration System(s) Where Energy is Recovered | Propylene | Ethylene & Propylene | — |
| 4. | Refrigeration Temperature Where Energy is Recovered, °F. | −40 | −75 | — |
| 5. | Vaporization Enthalpy, BTU/LB | 187.8 | 181.5 | Ref. 1 |
| 6. | Ethane Recycle Flow Rate, LB/HR | 103,910 | 103,910 | Table 1 and 2 |
| 7. | Vaporization Duty, MM BTU/HR | 19.5 | 18.9 | 5 × 6 |
| 8. | Ethylene Refrigerant Condensing Temperature, °F. | −30 | −30 | — |
| 9. | Ethylene Compressor Horsepower Saved By Vaporizer, HP/(MM BTU/HR) | — | 66 | Ref. 1 |
| 10. | Total Ethylene Compressor Horsepower Saved By Vaporizer, HP | — | 1247 | 7 × 9 |
| 11. | Condenser Duty/Ethylene Refrigeration Duty | NA | 1.17 | Ref. 1 |
| 12. | Ethylene Refrigeration Condenser Duty Saved By Vaporizer, MM BTU/HR | NA | 22.1 | 7 × 11 |
| 13. | Total Propylene Refrigeration Duty Saved By Vaporizer, MM BTU/HR | 19.5 | 22.1 | 7 and 12 |
| 14. | Propylene Refrigerant Condensing Temperature, °F. | 105 | 105 | — |
| 15. | Propylene Compressor Horsepower Saved By Vaporizer, HP/(MM BTU/HR) | 236 | 236 | Ref. 1 |
| 16. | Total Propylene Compressor Horsepower Saved By Vaporizer, HP | 4602 | 5216 | 13 × 15 |
| 17. | Total Compressor Horsepower Saved By Vaporizer | 4602 | 6463 | 10 + 16 |
| | Refrigeration Energy Recovery Calculation - Superheater | | | |
| 18. | Superheater Inlet Temperature, °F. | −46 | −77 | 2 |
| 19. | Superheater Outlet Temperature, °F. | 75 | 75 | — |
| 20. | Superheater Enthalpy, BTU/LB | 54 | 60 | — |
| 21. | Superheater Duty | 5.6 | 6.2 | 6 × 20 |
| 22. | Ethylene Refrigeration Horsepower Saving in Superheater | — | 86 | — |
| 23. | Propylene Refrigeration Horsepower Saving in Superheater | 773 | 1035 | — |
| 24. | Total Refrigeration Horsepower Saved By Superheating | 773 | 1121 | 22 + 23 |
| 25. | Total Refrigeration Horsepower Saved, Vaporizing + | 5375 | 7584 | 17 + 24 |

TABLE 3-continued

|  | Conventional | Invention | Source |
|---|---|---|---|
| Superheating |  |  |  |
| 26. Horsepower Saving | Base | 2209 | 25 |

Ref. 1:
Y. R. MEHRA, Chemical Engineering, p. 97, Dec. 18, 1978; p. 131, Jan. 15, 1979; and p. 95, Feb. 12, 1979.

Energy requirements for driving the recompressor 68 in the above example are estimated at 1290 horsepower, but a significant fraction of this power consumption is recovered as preheat energy in the ethane recycle stream flowing to the pyrolysis furnace, which in turn increases the amount of heat available in the pyrolysis furnace for steam generation or water preheating. In the above example, 3.6 MMBTU/hr. of preheat energy is recovered.

As is apparent to one skilled in the art from the description above, significant savings in capital and operating cost can be realized by applying the present invention to an ethylene plant design. By vaporizing ethane recycle stream 76 at low pressure, based upon a billion pounds per year ethylene plant, it is estimated about 20 MMBTU/hr. of process refrigeration duty utilizing $-77°$ F. ethylene refrigerant will be reduced. The process exchanger service normally served by the ethane recycle stream 76 vaporizing at high pressure is replaced with $-40°$ F. propylene refrigerant. The net result of such change is an estimated saving in total refrigerant compressor BHP of about 2200. This saving in compressor BHP is roughly equivalent to $2,300,000 in operating cost over three years assuming a fuel value of $4.0/MMBTU. This example does not assume optimization which would result in further savings. Aside from this saving in operational cost, the duty of ethylene condenser would be reduced by about 20 MMBTU/hr. This will permit a saving on capital expenditure because a smaller condenser can be utilized. Further, the lower compressor BHP will also save incremental capital investment on the two refrigeration compressors, their drivers, and a number of heat exchangers and drums in the refrigeration circuits.

In addition to the above savings, further savings can be achieved when a process according to the present invention utilizes an expander from treatment process 500 to drive the compressor 68. While an illustrative example of one such application is described below in connection with FIGS. 5 and 6, it would be apparent to one skilled in the art that other expanders or turbines, or a combination of expanders or turbines might also be utilized to drive compressor 68.

FIG. 5 is a flow diagram of a portion of the treatment process 500 depicted in FIG. 1. A demethanizer feed stream 80 is passed to a demethanizer 62 wherein a stream of ethylene and ethane 74 is recovered as a demethanizer bottom stream and a demethanizer overheads stream 81 is recovered from the demethanizer 62 and passed to a hydrogen separation process, generally depicted as 503, to recover a product stream of hydrogen 82 and a tail gas 83 which is passed to an expander generator 67 to produce electricity and an expanded tail gas stream 85. FIG. 6 is a flow diagram of a portion of the treatment process 500 depicted in FIG. 2 according to a preferred embodiment of the present invention wherein the expander 67 utilized in the treatment process 500 is utilized as a driver to the compressor 68.

Having fully described the present invention, it will be apparent from the above description and drawings that various modifications to the processes described herein may be made without departing from the scope of the present invention. Therefore, the invention is not intended to be limited except as may be required by the lawful scope of the following claims.

What is claimed is:

1. A process for recovering energy from an ethane-rich feed stream flowing to a pyrolysis furnace used for the production of ethylene from said feed stream, comprising the steps of:
    reducing the pressure of the ethane-rich stream to below the inlet pressure of the pyrolysis furnace to decrease the temperature of said ethane-rich stream to form a chilled ethane-rich stream;
    vaporizing the chilled ethane-rich stream by heat exchange with a process stream to form a vaporized ethane-rich stream and a chilled process stream;
    compressing the vaporized ethane-rich stream to form a compressed ethane-rich stream;
    passing the compressed ethane-rich stream to the pyrolysis furnace; and
    utilizing the chilled process stream to reduce refrigeration energy consumption.

2. A process as recited in claim 1 wherein the process stream is a refrigerant stream.

3. A process as recited in claim 1 wherein the ethane-rich stream is at a pressure between about 50 psia to about 350 psia.

4. A process as recited in claim 1 comprising the further step of recovering the ethane-rich stream from a $C_2$ splitter.

5. A process as recited in claim 1 wherein the chilled process stream is at a temperature lower than $-50°$ F.

6. A process as recited in claim 1 wherein the vaporized ethane-rich stream is compressed by a compressor which utilizes an expander as a driver.

7. A process as recited in claim 1 wherein the ethane-rich stream originates in a plant in which the pyrolysis furnace is located.

8. A process as recited in claim 1 wherein the ethane-rich stream originates in a different plant than the plant in which the pyrolysis furnace is located.

9. A process as recited in claim 1 wherein the ethane-rich stream contains at least 80 mole percent ethane.

10. A process as recited in claim 1, wherein the ethane-rich stream mixes with at least one feed stream prior to being vaporized.

11. A process as recited in claim 1 wherein the ethane-rich stream mixes with at least one feed stream following vaporization.

12. A process as recited in claim 1 wherein the ethane-rich stream is superheated by heat exchange with a second process or stream after being vaporized.

13. A process as recited in claim 12 wherein the second process stream is a refrigerant stream.

14. A process as recited in claim 12 wherein the first process stream and the second process stream are the same.

15. A process as recited in claim 1 wherein the inlet pressure of the pyrolysis furnace is generally in the range of 50 to about 130 psia.

16. A process as recited in claim 1 wherein the ethane-rich stream is reduced to a pressure range from about 14 psia to about 90 psia.

17. A process as recited in claim 1 wherein the process stream is comprised of a demethanizer feed stream.

18. A process as recited in claim 12 wherein the ethane-rich stream contains at least 80 percent ethane.

19. A process for recovering energy from a feed stream rich in ethane, comprising the steps of:
   passing a feed stream to a pyrolysis furnace at an inlet pressure of the pyrolysis furnace;
   cracking the feed stream in the pyrolysis furnace to form a cracked stream;
   passing the cracked stream through a treatment process to form a stream comprised of ethylene and ethane;
   passing the stream comprised of ethylene and ethane to a $C_2$ splitter;
   recovering an ethylene product stream from the $C_2$ splitter;
   recovering an ethane-rich recycle stream from the $C_2$ splitter;
   reducing the pressure of the ethane-rich recycle stream below the inlet pressure of the pyrolysis furnace to decrease the temperature of said ethane-rich recycle stream to form a chilled ethane-rich recycle stream;
   vaporizing the chilled ethane-rich recycle stream by heat exchange with a process stream to form a vaporized ethane-rich recycle stream used for the production of ethylene by pyrolysis and a chilled process stream;
   compressing the vaporized ethane-rich recycle stream to the inlet pressure of the pyrolysis furnace to form a compressed ethane-rich recycle stream; and
   passing the compressed ethane-rich recycle stream to the pyrolysis furnace.

20. A process as recited in claim 19 wherein the process stream is a refrigerant stream.

21. A process as recited in claim 19 wherein the chilled process stream is utilized to reduce an overall energy consumption for the production of the ethylene product stream.

22. A process as recited in claim 19 wherein the inlet pressure of the pyrolysis furnace is generally in the range of about 50 to about 130 psia.

23. A process as recited in claim 22 wherein the ethane-rich recycle stream is reduced to a pressure range from about 14.0 psia to about 90 psia.

24. A process as recited in claim 19 wherein the treatment process utilizes a cascade refrigeration system to provide chilling.

25. A process as recited in claim 19 wherein the chilled process stream is at a temperature lower than −50° F.

26. A process as recited in claim 19 wherein the vaporized ethane-rich recycle stream is compressed by a compressor which utilizes an expander as a driver.

27. A process as recited in claim 26 wherein the expander is also utilized in the treatment process.

28. A process as recited in claim 19 wherein the vaporized ethane-rich recycle stream is superheated by heat exchange with a second process stream.

29. A process as recited in claim 28 wherein the second process stream is a refrigerant stream.

30. A process as recited in claim 28 wherein the first process stream and the second process stream are the same.

31. A process as recited in claim 19 wherein the stream comprised of ethylene and ethane is at least 90 mole percent ethylene and ethane.

32. A process as recited in claim 19 wherein the ethane recycle stream is comprised of at least 80 mole percent ethane.

33. A process as recited in claim 19 wherein the process stream is comprised of a demethanizer feed stream.

34. A process as recited in claim 19 wherein the ethane recycle stream mixes with at least one ethane-rich feed stream prior to being vaporized.

35. A process as recited in claim 19 wherein the ethane recycle stream mixes with at least one pyrolysis furnace feed stream following vaporization.

36. A process as recited in claim 19 wherein the chilled process stream is used in the treatment process to reduce refrigeration energy consumption.

37. An improved process for producing ethylene wherein a feed stream is cracked in a pyrolysis furnace and passed to a treatment process to form a stream comprised of ethylene and ethane which is passed to a $C_2$ splitter to form an ethylene product stream and an ethane-rich recycle stream, the improvement comprising the steps of:
   reducing the pressure of the ethane-rich recycle stream to decrease the temperature of said ethane-rich recycle stream to form a chilled ethane-rich recycle stream;
   vaporizing the chilled ethane-rich recycle stream by heat exchange with a first process stream to form a vaporized ethane recycle stream and a first chilled process stream;
   superheating the vaporized ethane-rich recycle stream by heat exchange with a second process stream to form a superheated ethane-rich recycle stream and a second chilled refrigerant stream;
   compressing the superheated ethane-rich recycle stream to an inlet pressure of the pyrolysis furnace to form a compressed ethane-rich recycle stream, and
   passing the compressed ethane-rich recycle stream to the pyrolysis furnace.

38. An improved process as recited in claim 37 wherein the first and the second process streams are the same.

39. An improved process as recited in claim 37 wherein at least one of the first and the second process streams is a refrigerant stream.

40. A process as recited in claim 37 wherein the chilled ethane-rich recycle stream is at a pressure in a pressure range from about 14.0 psia to about 90 psia.

41. A process as recited in claim 37 wherein the vaporized ethane-rich recycle stream is compressed by a compressor which utilizes an expander as a driver.

42. A process as recited in claim 37, wherein the expander is also utilized in the improved process.

43. A process as recited in claim 37, wherein the chilled process stream is at a temperature lower than −50° F.

44. A process as recited in claim 37, wherein the ethane-rich stream is comprised of at least 80 mole percent ethane.

45. A process as recited in claim 37 wherein the first chilled process steam is used in the treatment process to reduce refrigeration energy consumption.

46. A process as recited in claim 37, wherein the ethane-rich stream mixes with at least one pyrolysis furnace feed stream prior to being vaporized.

47. A process as recited in claim 37, wherein the ethane-rich stream mixes with at least one pyrolysis furnace feed stream following vaporization.

48. A process as recited in claim 37, wherein the inlet pressure of the pyrolysis furnace is generally in the range of about 50 to about 130 psia.

49. An improved process for producing ethylene by pyrolysis in an olefin plant wherein a feed stream is passed to a pyrolysis furnace at an inlet pressure of the pyrolysis furnace wherein the feed stream is cracked to form a cracked stream which is passed to a treatment process which utilizes a cascade refrigeration system, a demethanizer and a $C_2$ splitter to form a plurality of fractionated streams including at least one demethanizer feed stream which is passed to the demethanizer wherein a stream comprised of ethylene and ethane is recovered as a demethanizer bottom stream which is passed to the $C_2$ splitter to form an ethylene product stream collected as a $C_2$ splitter overheads stream and an ethane-rich recycle stream collected as a $C_2$ splitter bottoms stream, the stream comprised of ethylene and ethane containing at least 90 mole percent ethylene and ethane and the ethane-rich recycle stream being comprised of at least 80 mole percent ethane, the improvement comprising the steps of:
 reducing the pressure of the ethane-rich recycle stream to decrease the temperature of said ethane-rich recycle stream to form a chilled ethane-rich recycle stream;
 vaporizing the chilled ethane-rich recycle stream by heat exchange with a first process stream to form a vaporized ethane-rich recycle stream and a chilled process stream;
 superheating the vaporized ethane-rich recycle stream by heat exchange by a second process stream to form a superheated ethane-rich recycle stream and a second chilled process stream;
 compressing the superheated ethane-rich recycle stream to the inlet pressure of the pyrolysis furnace by a compressor to form a compressed ethane-rich recycle stream; and
 passing the compressed ethane-rich recycle stream to the pyrolysis furnace.

50. An improved process as recited in claim 49 wherein the inlet pressure of the pyrolysis furnace is generally in the range of about 50 to about 130 psia and the chilled ethane recycle stream is generally in a pressure range from about 14.0 psia to about 90 psia.

51. An improved process as recited in claim 49 wherein the chilled ethane-rich recycle stream is vaporized in a demethanizer feed chiller.

52. An improved process as recited in claim 49 wherein the first and the second process stream are the same.

53. An improved process as recited in claim 49 wherein at least one of the first and the second process streams are a refrigerant stream.

54. An improved process as recited in claim 49 wherein the chilled process stream is used in the treatment process to reduce refrigeration energy consumption.

55. A process for producing ethylene by pyrolysis in an olefin plant, comprising the steps of:
 passing a feed stream to a pyrolysis furnace at an inlet pressure generally in the range of about 50 to about 130 psia;
 cracking the feed stream in the pyrolysis furnace to form a cracked stream;
 passing the cracked stream to a treatment process which utilizes a cascade refrigeration system, a demethanizer and a $C_2$ splitter to form a plurality of fractionated streams including at least one demethanizer feed stream;
 passing at least one demethanizer feed stream to a demethanizer wherein a stream comprised of at least 90 mole percent ethylene and ethane is recovered as a demethanizer bottom stream;
 passing the demethanizer bottom stream to a $C_2$, splitter;
 collecting an ethylene product stream as a $C_2$ splitter overheads stream;
 collecting an ethane-rich recycle stream comprised of at least 80 mole percent ethane as a $C_2$ splitter bottoms stream;
 reducing the pressure of the ethane-rich recycle stream below the inlet pressure to decrease the temperature of said ethane-rich recycle stream to form a chilled ethane-rich recycle stream within the pressure range from about 14.0 psia to about 90 psia;
 vaporizing the chilled ethane-rich recycle stream by heat exchange with a process stream at a temperature lower than $-50°$ F. to form a vaporized ethane-rich recycle stream and a chilled process stream;
 compressing the vaporized ethane-rich recycle stream to the inlet pressure to form a compressed ethane-rich recycle stream;
 passing the compressed ethane-rich recycle stream to the pyrolysis furnace; and
 utilizing the chilled process stream in the treatment process.

56. A process as recited in claim 55 wherein the process stream is comprised of a demethanizer feed stream.

* * * * *